United States Patent [19]

Benigni et al.

[11] 4,082,760

[45] Apr. 4, 1978

[54] DERIVATIVES OF 2H,3H-BENZIMIDAZO(1,2-b)OXAZOLE

[75] Inventors: Fulvio Benigni, Milan; Lucio Trevisan, Ferrara, both of Italy

[73] Assignee: Italchemi S.p.A. Istituto Chimico Farmaceutico, Milan, Italy

[21] Appl. No.: 638,038

[22] Filed: Dec. 5, 1975

[51] Int. Cl.$^2$ ............................................ C07D 498/14
[52] U.S. Cl. ........................ 260/307 FA; 260/293.58;
260/348.44; 260/348.46; 260/348.48;
260/348.49; 260/348.57; 260/348.58;
424/248.4; 424/267; 424/272; 424/248.57;
544/129; 544/130; 544/137; 548/327; 548/329;
424/248.54; 424/248.53; 424/248.55;
424/248.56; 424/248.58
[58] Field of Search ................. 260/307 FA; 424/272

[56] References Cited

U.S. PATENT DOCUMENTS 3,264,319   8/1966   Kamal .................................. 260/307

OTHER PUBLICATIONS

Benigni et al., Il Farmaco–Ed. Sc., vol. 29, pp. 936–940 (1974).
Morrison et al., "Organic Chemistry", Allyn and Bacon, Inc. (1959) pp. 367, 423.

*Primary Examiner*—Raymond V. Rush
*Attorney, Agent, or Firm*—Stevens, Davis, Miller & Mosher

[57] ABSTRACT

Derivatives of 2H, 3H-benzimidazo (1,2-b) oxazole have the property of inhibiting the beta-lactamase produced by many germs resistant to penicillins and cephalosporins, and may be used in mixture with these antibiotics to increase their activity.

3 Claims, No Drawings

DERIVATIVES OF 2H,3H-BENZIMIDAZO(1,2-b)OXAZOLE

This invention relates to the synthesis of derivatives of 2H, 3H-benzimidazo (1,2-b) oxazole of general formula (I):

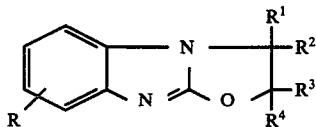

in which R, $R^1$, $R^2$, $R^3$, $R^4$, which may be equal or different, represent H, alkyl, aryl, $(CH_2)_n$-halogen, $(CH_2)_n$—$COOR^5$, $(CH_2)_n$—CHO, $(CH_2)_n$—$COR^5$, $(CH_2)_n$—$N(R^5)_2$, $(CH_2)_n$—OH, $(CH_2)_n$—$NO_2$, $(CH_2)_nO$—$R^5$, $(CH_2)_n$—$CON(R^5)_2$, $(CH_2)_n$—CN,

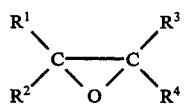

$R^5$ = H, alkyl of low molecular weight, or aryl; $N(R^5)_2$ may also represent a heterocyclic 5- or 6-membered ring, which may contain another heteroatom: for instance, $N(R^5)_2$ may represent a pyrrolidino, piperidino or morpholino group; $n + 0, 1, 2, 3$.

These products are obtained by reacting an alkali salt of 2-chlorobenzimidazole (or of its derivatives in which R has the meaning given heretofore) with compounds of general formula (II):

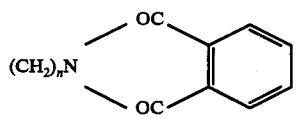

in which $R^1$, $R^2$, $R^3$, $R^4$ have the meaning already stated. The reaction is carried out by mixing the two reagents at a temperature between 0° and 100° and leaving them in contact for some hours. An organic solvent may be used if desired for diluting the reaction mixture. During the reaction an intermediate is formed of general formula (III):

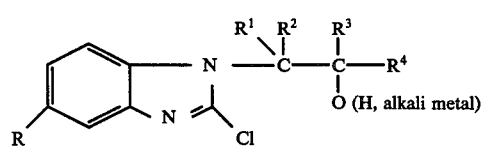

in which R, $R^1$, $R^2$, $R^3$, $R^4$ have the meanings already stated.

This intermediate is then transformed into the products of general formula I.

In some cases these intermediates have been isolated and then transformed into the corresponding products of general formula I by boiling with hydroxides or alkali alcoholates in an aqueous or alcoholic solution.

Alternatively, an alkali salt of 2-chlorobenzimidazol may be reacted with compounds of general formula (IV):

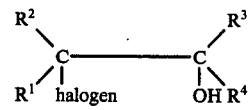

in which $R^1$, $R^2$, $R^3$, $R^4$ have the meanings already stated.

Products of general formula (III) are obtained with very low yields, and may then be transformed into compounds of general formula (I) by boiling with hydrates or alkali alcoholates in an aqueous or alcoholic solution.

Products of general formula (I) are transformed by boiling in concentrated hydrochloric acid into products of general formula (V):

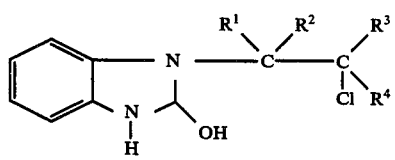

from which the products of general formula (I) may be again obtained by boiling with alkali.

Products of general formula (I) have the property of inhibiting the beta-lactamase produced by many germs resistant to penicillins and cephalosporins. In fact, the prolonged use of these antibiotics has given rise to the selection of germs resistant to them. Their resistance is explained by the production of enzymes (beta-lactamase) which, by hydrolising the beta-lactam bond of penicillins and cephalosporins make these antibioties inactive.

The capacity of the products of general formula (I) to compete with the action of the beta-lactamase may be shown by comparing the minimum inhibiting concentrations (MIC) of some penicillins and cephalosporins when mixed with equimolar quantities of the products of general formula I and when not so mixed, in relation to pathogenic germs which produce beta-lactamase.

| | MIC (in γ/cc) | | | | | |
|---|---|---|---|---|---|---|
| | A | B | C | D | E | F |
| Escherichia Coli R9 | 500 | 250 | 1000 | 500 | | |
| Escherichia Coli R8 | 500 | 250 | | | | |
| Protetts mirabilis R7 | 1000 | 250 | | | | |
| Protetts mirabilis | 1000 | 1000 | | | | |
| Protetts Rettgeri R5 | 1000 | 125 | | | | |
| Pseudomonas Aeruginosa R4 | 1000 | 500 | 1000 | 500 | | |
| Escherichia Coli R3 | 1000 | 500 | | | | |
| Protetts mirabilis R2 | 1000 | 1000 | | | | |
| Pseudomonas Aeruginosa R1 | | | | | 1000 | 250 |

A = Ampicillin
B = Ampicillin + 2-chloromethyl-2H,3H-benzimidazo(1,2-b)oxazole
C = Cephalothin
D = Cephaloidin + 2-chloromethyl-2H,3H-benzimidazo(1,2-b)oxazole
E = Cephaloridine
F = Cephaloridine + 2-chloromethyl-2H,3H-ben imida o(1,2-b)oxa ole The products of general formula (I) may be used, in mixture with penicillins or cephalosporins, to increase the activity of these antibiotics. The mixtures may be used for preparing any suitable pharmaceutical form such as injectable phials, tablets, sugar-coated pills, ointments, suppositories, capsules etc.

Some non-limiting examples of the present invention are given hereinafter.

EXAMPLE 1

1-(2-hydroxybutyl)-2-chlorobenzimidazole 5 g of the sodium salt of 2-chlorobenzimidazole are suspended in 50 ml of epoxybutane in a flask provided with a reflux condenser and a $CaCl_2$ plug. The mixture is boiled for 15 hours, the epoxybutane is then evaporated under vacuum and the residue is taken up with water and made alkaline with 10% sodium hydrate. After agitation for about 1 hour it is filtered and the residue obtained is crystallised twice from benzene. A white product is obtained which melts at 126°.

The I.R. spectrum presents band at 3270, 1615, 1600 $cm^{-1}$. M.W. 224.5.

Found %: C, 58.64; H, 5.90; N, 12.70. For $C_{11}H_{13}ClN_2O$—Calc. %: C, 58.80; H, 5.79; N, 12.47.

EXAMPLE 2

2-ethyl-2H,3H-benzimidazo(1,2-b)-oxazole 2.55 g of 1-(2-hydroxybutyl)-2-chlorobenzimidazole and 1 g of NaOH are dissolved in 300 ml of a: 1:1 ethanol:$H_2O$ mixture. It is boiled under reflux for 12 hours, then part of the alcohol is evaporated and the remainder is diluted with water. A white product precipitates, which is filtered, dried and crystallised from benzene. M.P. 105°–107°.

The I.R. spectrum presents bands at 1635, 1590 $cm^{-1}$. M.W. 188.

Found %: C, 70.22; H, 6.48; N, 15.10. For $C_{11}H_{12}N_2O$—Calculated %: C, 70.21; H, 6.38; N, 14.89. R.M.N. spectrum ($CDCl_3$):τ2.5 (m, 1H, arom.), 2.9 (m, 3H, arom.) 4.75 (q, 1H, —O—CH—$CH_2$), 5.75–6.1 (t, 1H-t, 1H, N—$CH_2$—), 8.1 (q, 2H, $CH_2$—$CH_3$) 8.9 (t, 3H, $CH_2$—$CH_3$).

EXAMPLE 3

2-chloromethyl-2H,3H-benzimidazo-(1,2-b)-oxazole 5 g of the sodium salt of 2-chlorobenzimidazole are mixed with 45 ml of epichlorhydrin and the mixture is agitated overnight at ambient temperature.

The epichlorhydrin is evaporated under vacuum, the residue is taken up with water and alkalised with 10% NaCH.

It is extracted with benzene and the organic phase is concentrated to a small volume after washing with water and drying.

After siome hours a white product precipitates which is recrystallised from benzene. The product is in the form of white shiny flakes, melts at 136°–138°, and contains Cl and N.

The I.R. spectrum presents bands at 1635 and 1590 $cm^{-1}$. M.W. 208.5

Found %: C, 57.27; H, 4.39; N, 13.50; Cl. For $C_{10}H_9ClN_2O$—Calculated %: C, 57.55; H, 4.32; N, 13.43; Cl, 17.03. R.M.N. spectrum ($CDCl_3$):τ2.5 (m, 1H, arom.), 2.9 (m, 3H, arom.) 4.6 (q, 1H, C—CH—$CH_2$), 5.71–6.1 (m, 2H-t, 2H, N—$CH_2$—CH and —$CH_2$—Cl).

EXAMPLE 4

2-hydroxymethyl-2H,3H-benzimidazo-(1,2-b)-oxazole 15 g of the sodium salt of 2-chlorobenzimidazole are suspended in 50 ml of benzene; 15 ml of glycidol at ambient temperature are added to the agitated suspension. It is left under agitation overnight and then water and sodium hydrate are added. It is shaken. A white precipitate is formed which is collected and crystallised from 95% ethanol. M.P. 192°–193° C. I.R. spectrum: bands at 3160, 1635, 1590 $cm^{-1}$.

EXAMPLE 5

2-carbethoxy-3-methyl-2H,3H-benzimidazo-(1,2-b)-oxazole 4,5 g of the sodium salt of 2-chlorobenzimidazole are suspended in 20 ml of benzene; 15 ml of 2,3 epxoybutyrate of ethyl are added to the suspension, which is then left under agitation at ambient temperature for 2 days.

Water and sodium hydrate are added, it is shaken and the benzene solution is separated, and then concentrated to 2–3 ml. The residue is chromatographed over a silica gel column, with 9:1 benzene-ethanol as eluent.

After an initial fraction, the fraction containing the 2-carbethoxy-3-methyl-2H,3H-benzimidazo-(1,2-b)-oxazole passes.

The solvent is evaporated and an oily residue is obtained which is recrystallised from benzene. M.P. 147°–148° C.

I.R. spectrum: bands at 1755, 1635, 1590 $cm^{-1}$.

EXAMPLE 6

1-(2-hydroxyethyl)-2-chlorobenzimidazole 5 g of the sodium salt of 2-chlorobenzimidazole are suspended in 50 ml of benzene. 2 ml of ethylene oxide are added and the mixture is left under agitation for 1 day.

Water and sodium hydrate are added, and the insoluble residue is filtered, which is crystallised from benzene.

M.P. 135°–136° C.

I.R. spectrum: bands at 3300, 1615, 1600 $cm^{-1}$.

EXAMPLE 7

2H,3H-benzimidazo-(1,2-b)-oxazole 2 g of the product obtained in example 6 are suspended in 100 ml of 1:1 water-alcohol mixture. 1.5 g of NaOH are added and it is refluxed for one night.

The ethanol is evaporated, water is added and the precipitate obtained is filtered.

It is crystallised from benzene.
M.P.: 104°–105° C.
I.R. spectrum: bands at 1635, 1590 $cm^{-1}$.

EXAMPLE 8

2-(N-morpholinomethyl)-2H,3H-benzimidazo-(1.2-b)-oxazole, 5 g of the sodium salt of 2-chlorobenzimidazole are suspended in 50 ml of benzene and 5 g of 2,3-epoxymorpholine are added to the suspension, which is then stirred at room temperature for 3 days. The solvent is then evaporated to dryness, water is added, the solution is saturated with NaCl and extracted with benzene. The benzene solution is concentrated to a small volume; the concentrated solution is left overnight at 0°–5° C. A white product, m.p. 147°–148° C is obtained.

The I.R. spectrum presents bands at 1630, 1590, 1550 $cm^{-1}$ M.W. 259

Found %: C, 64,76; H, 6,54; N, 16,19. For $C_{14}H_{17}N_3O_2$—Calculated %: C, 64,86; H, 6,56; N, 16,22.

We claim:
1. 2H,3H-benzimidazo-(1,2-b)oxazole.
2. 2-hydroxymethyl-2H,3H-benzimidazo-(1,2-b)oxazole.
3. 2-carbethoxy-3-methyl-2H,3H-benzimidazo-(1,2-b)oxazole.

* * * * *